United States Patent [19]

Smith

[11] 4,278,078
[45] Jul. 14, 1981

[54] LAVAGE HANDPIECE

[75] Inventor: William E. Smith, Charleston Township, Kalamazoo Country, Mich.

[73] Assignee: Stryker Corporation, Kalamazoo, Mich.

[21] Appl. No.: 124,893

[22] Filed: Feb. 26, 1980

[51] Int. Cl.³ .............................................. A61H 9/00
[52] U.S. Cl. ...................................... 128/66; 128/229
[58] Field of Search ............. 128/66, 229, 230, 214 F, 128/234; 417/412, 476, 477

[56] References Cited

U.S. PATENT DOCUMENTS

| 1,970,626 | 8/1934 | Rockwell | 103/150 |
| 3,227,158 | 1/1966 | Mattingly | 128/66 |
| 3,653,377 | 4/1972 | Rebold | 128/66 |
| 3,674,024 | 7/1972 | Cirillo | 128/234 |
| 3,863,628 | 2/1975 | Vit | 128/66 |
| 3,960,466 | 6/1976 | Taylor | 128/66 X |
| 3,993,054 | 11/1976 | Newman | 128/66 |

Primary Examiner—John D. Yasko
Attorney, Agent, or Firm—Blanchard, Flynn, Thiel, Boutell & Tanis

[57] ABSTRACT

Therapeutic device for providing intermittent flow of liquid to an incision or wound. A handpiece containing a suitable motor is supportingly connected to a pump unit containing a reciprocable plate. Operating means connect said motor to said plate for effecting reciprocation thereof in a direction perpendicular to the plane of the plate. A resiliently flexible tube extends through said pumping unit and adjacent said plate and is subjected to peristaltic pumping action as said plate reciprocates, thereby urging liquid within said tube to move intermittently therethrough. One end of the tube is connected to a source of liquid and the other end is connected to a suitable nozzle for directing such liquid into the wound or incision.

10 Claims, 5 Drawing Figures

LAVAGE HANDPIECE

FIELD OF THE INVENTION

This invention relates in general to an apparatus referred to as a therapeutic lavage, for producing a pulsating flow of liquid from a source thereof through a tube for irrigating or washing a wound or incision in flesh, as during the performance of surgery.

BACKGROUND OF THE INVENTION

In the treatment of tissue, both externally and within an incision or wound, it has been known that a controllable pulsating stream of liquid provides a therapeutic action which is desirable in promoting prompt and correct healing. Thus, devices such as that shown in the patent to Gordon Arthur Newman, U.S. Pat. No. 3,993,054, and assigned to the same assignee as the present application, have been developed broadly for this purpose. Another device of this type, but developed specifically for use in oral hygiene, is disclosed in U.S. Pat. No. 3,227,158, issued Jan. 4, 1966.

The devices for such purposes prior to that of the Newman patent were in general effective to solve some of the problems in the art but certain problems still remained which it was the purpose of the Newman disclosure to meet. Particularly where surgical sterility was desired, it was difficult at best with some of the prior known apparatus to sterilize same sufficiently after, for example, use thereof in irrigating an infected wound or an incision in infectious tissue. Also, much of the prior existing equipment for this purpose was complicated, hence expensive in construction, and it lacked a simple and inexpensive means for controlling the flow of the pulsating liquid from the apparatus.

Some of these problems were solved by the device of said Newman patent, particularly those regarding ease of sterilization and ease of control, but the device there shown is relatively heavy and was neither designed for nor capable of easy transport from one location of use to another nor was it capable of easy manual manipulation which was required in some types of use.

Accordingly, the major objects of the invention include:

1. The provision of a therapeutic lavage capable of producing a manually controllable pulsating stream of liquid which lavage is relatively simple in construction and small enough for effective and convenient manual manipulation.

2. To provide a device, as aforesaid, in which all of the parts of said lavage can be sterilized after said lavage is used on a patient or some of said parts can be sterilized and/or others of said parts can be readily and quickly removed therefrom for disposal and replacement as desired.

3. To provide apparatus, as aforesaid, which will be of relatively simple construction and hence not excessively expensive.

4. To provide apparatus, as aforesaid, which will be capable of long and reliable use with a minimum of maintenance.

5. To provide apparatus, as aforesaid, which will not require electrically driven equipment and thereby eliminate the expense and danger associated with such equipment when used in an operating room.

Other objects and purposes of this invention will become apparent to persons familiar with this type of equipment upon reading the following specification and inspection of the accompanying drawings.

DETAILED DESCRIPTION

Figure 1:
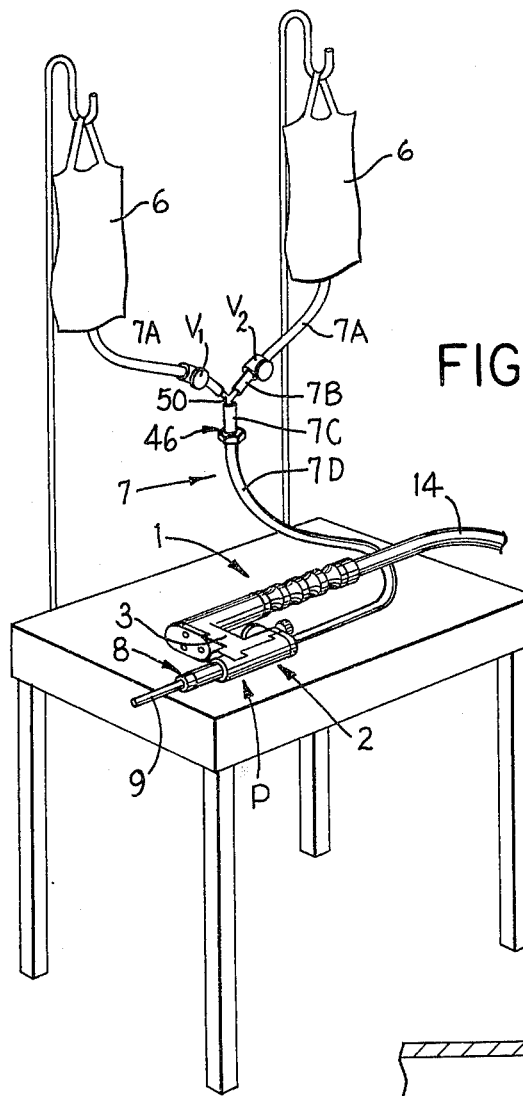
FIG. 1 illustrates the apparatus of the invention at rest upon a suitable table and associated with a plurality of containers containing a supply of liquid which is furnished to the apparatus.

Turning now to the apparatus comprising the illustrated embodiment of the invention, there is shown in FIG. 1 conventional means for supporting one or more liquid receiving containers 6 at a point sufficiently above a pump unit P to provide a substantial head on the upstream side thereof, tubing 7 connecting said containers through valves $V_1$ and $V_2$ first to the pump unit P and thence through the check valve 8 to a nozzle 9 by which liquid from one or both of the containers 6 as desired is guided to or into the wound, incision or other feature being treated. This general assembly is already known in the art and sufficiently illustrated in the above-mentioned Pat. No. 3,993,054.

Turning now to the details of the pump unit P comprising the present invention, there is shown in the drawings a hand grip portion 1 containing the motive means hereinafter further described, a housing 2 containing pump and flow control means hereinafter further described and a connecting portion 3 by which the hand grip 1 is connected operatively to the housing 2.

Figure 2:
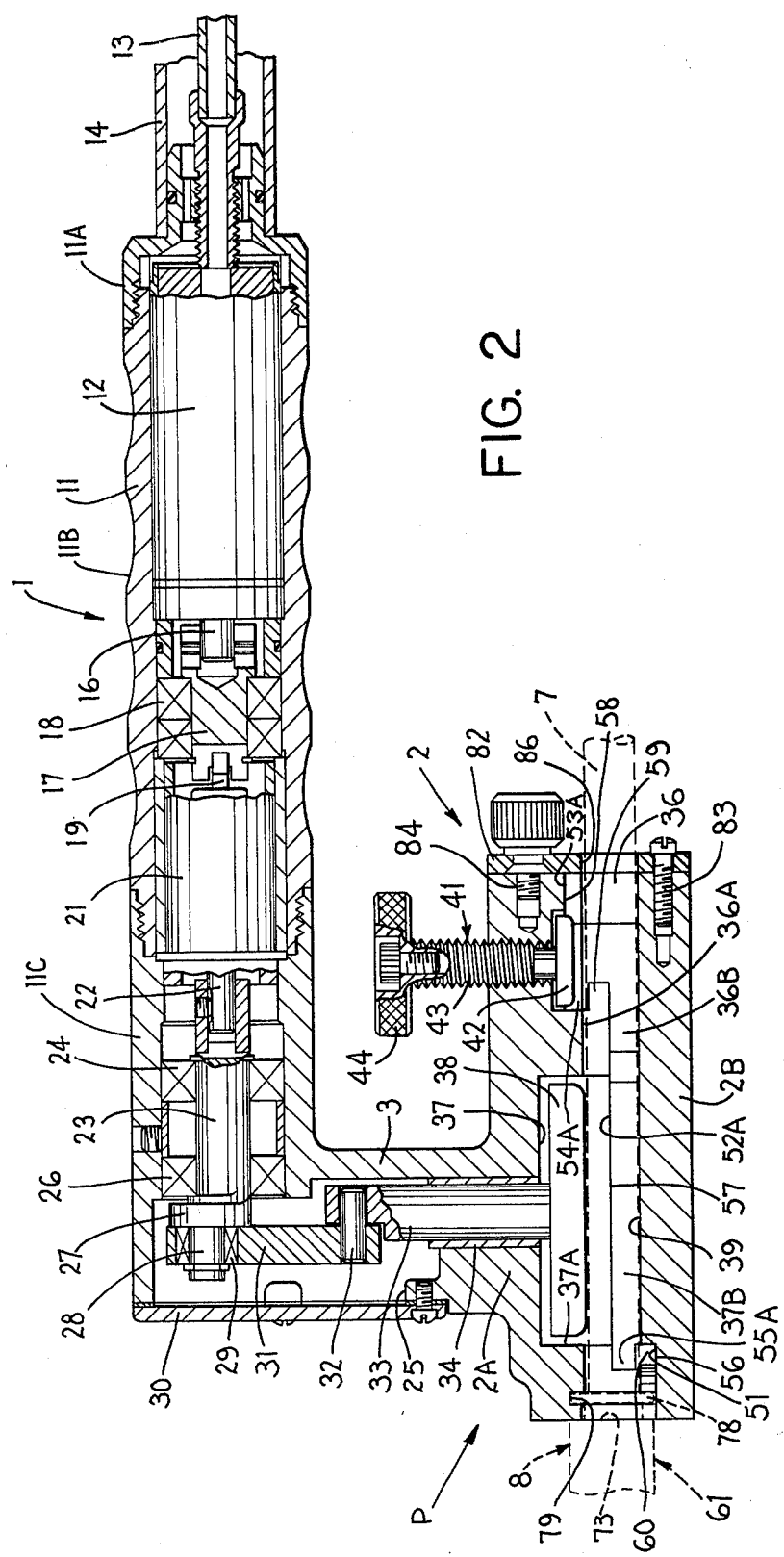
FIG. 2 is a central sectional view of apparatus embodying the invention.

Referring now to FIG. 2, the hand grip portion 1 comprises a generally tubular structure 11 in which is located a motor 12. For assembly purposes, said hand grip portion 1 may be divided into threadedly connected components as desired, here components 11A, 11B and 11C. Said motor is preferably an air motor of conventional form in order to eliminate the necessity for electrical connections which are for known reasons undesirable in an operating room. In this instance, a conventional air inlet conduit 13 is provided for supplying said motor and an exhaust conduit 14 concentric with the inlet conduit 13 is provided in a conventional and known manner. The output shaft 16 of said motor is fixed to a suitable and conventional coupling 17, same being supported in a desired manner on bearings 18 and drives the input shaft 19 of a conventional speed changer, usually speed reducer, 21. The output shaft 22 thereof is connected to a shaft 23 which is supported by suitably spaced bearings 24 and 26 for driving an eccentric 27. A pin 28 on said eccentric is connected through a suitable bearing 29 to a connecting drive link 31 and pin 32 to the vertically reciprocable plunger 33. An access opening 25 is conveniently provided as shown and closed by a removably fastened closure plate 30.

Said plunger 33 and drive link 31 are received at least partially within the connecting portion 3 as shown in the drawings and the plunger 33 is further mounted for vertical reciprocation in the sleeve 34 which is in turn mounted partially within the connector 3 and partially within the housing 2.

Said housing 2 (FIG. 2) is fixed to the lower end of the connector 3 and is provided with a passageway 36 extending lengthwise therethrough. Intermediate the ends of said passageway is a pumping chamber 37 which contains a pump plate 38 secured to the lower end of the plunger 33 whereby operation of the motor 12 will act through speed changer 21, shaft 23, link 31 and plunger 33 to reciprocate the plate 38 toward and away from the surface 39 opposite said plate. Thus, the resiliently flexible tubing 7 extending through the opening 36 will be alternately compressed and released by reciprocation of the plate 38 in a manner characteristic of peristaltic pumps.

Figure 5:
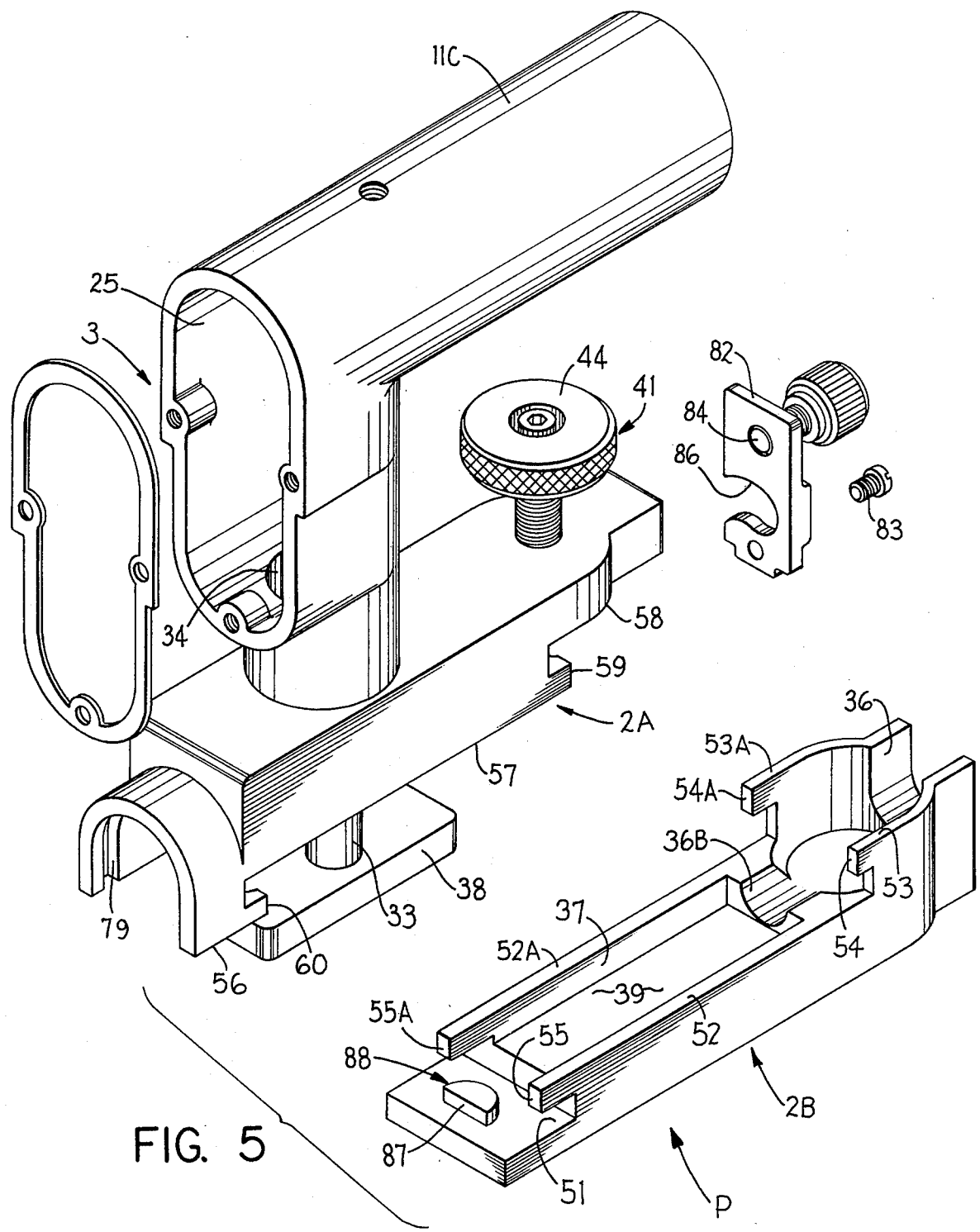
FIG. 5 is an oblique exploded view of the major constituents of the apparatus of FIG. 2.

While broadly the housing 2 (FIG. 2) may be designed in any of several forms to provide for ready insertion thereinto of the flexible tubing 7, the form shown in the drawings has been found particularly advantageous and forms a portion of at least the narrower aspects of the invention. In this embodiment, said pump unit 2 is divided longitudinally into an upper component 2A and a lower component 2B. Said lower component 2B (FIG. 5) is provided with three, upwardly facing, stepped surfaces 51, 52–52A and 53–53A.

The upper surfaces 53 and 53A are separated by a portion of the passageway 36 and extended by two projections 54 and 54A which are parallel with and spaced above the middle surfaces 52 and 52A which are separated by the lower part of the pumping chamber 37. Two projections 55 and 55A, which are spaced above the lower surface 51, extend said middle surfaces 52 and 52A.

The upper portion 2A has three stepped downwardly facing surfaces and projections, some of which are indicated at 56, 57, 58, 59 and 60, arranged for interlocking engagement with the surfaces and projections 51, 52, 53, 54 and 55, respectively, on the lower portion 2B, as appearing in FIG. 2.

The pump chamber 37 (FIG. 2) is here contained partly in the upper portion 2A as indicated at 37A and partly in the lower portion 2B as indicated at 37B. The rightward (as appearing in FIG. 2) end of passageway 36 is defined entirely within the lower portion 2B whereas the leftward end thereof is defined entirely within the upper portion 2A. Part of said passageway 36 rightwardly of the chamber 37 is located partially in the upper part 2A as indicated at 36A and partially in the lower portion 2B as indicated at 36B.

An end plate 82 is fixed by a screw 83 to the right end of the lower portion 2B and is also secured to the upper portion 2A by a manually operable screw 84. An opening 86 is provided in the plate 82 for the passage therethrough of the tube 7. Thus, when the parts 2A and 2B are assembled, as shown in FIG. 2, same may be quickly locked in place by appropriate rotation of the screw 84. When it is desired to replace the tube 7, same may be quickly accomplished by loosening the screw 84 and separating the portion 2B from the portion 2A.

In the illustrated embodiment, there is positioned upstream of the chamber 37 a volume control valve 41 comprising a pad 42 connected for movement with a screw 43 in response to rotation of a knurled handle 44. Rotation of said knurled handle 44 in an appropriate direction moves the pad 42 upwardly or downwardly against the tubing 7 thereby partially opening or closing same to a selectable extent for controlling the volume of liquid passing therethrough. This volumetric control, while preferred, is nevertheless a refinement which may be omitted if desired.

Figure 4:
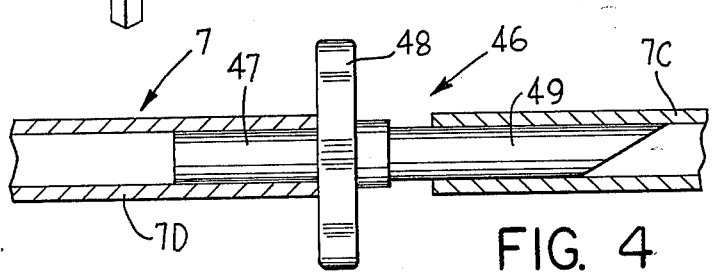
FIG. 4 illustrates one convenient and conventional means for associating the flexible tube with a source of liquid.

The upstream end of said tubing 7 has fitted thereto any desired fitting means for operative connection of said tubing 7 with one or both of the containers 6. Such connection here comprises a connecting unit 46 (FIG. 4) having a tube 47 for insertion into the portion 7D of said tubing 7, a flange 48 for limiting such insertion and a further tube 49 constituting a continuation of the tube 47 projecting into the portion 7C of the tubing 7. Said portion 7C is then connected in this embodiment (FIG. 1) through a Y-shaped connector 50 to the valves $V_1$ and $V_2$ thence through tubes 7A to the bottoms of the respective containers 6. Thus, by proper manipulation of said valves $V_1$ and $V_2$ the contents of the containers 6 may be fed either simultaneously or successively as desired to the pump unit P.

Figure 3:
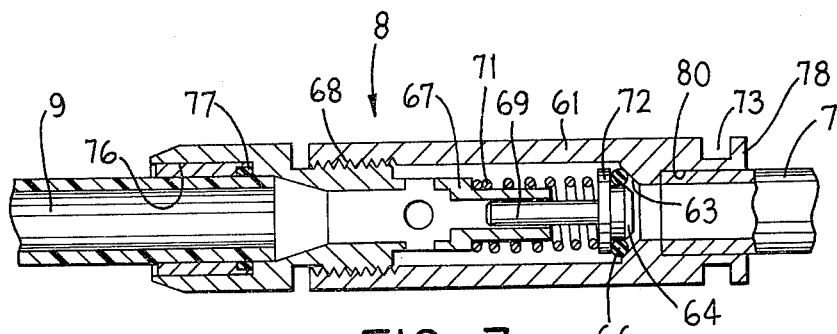
FIG. 3 is a central sectional view of a check valve as used in association with the apparatus of FIG. 2.

Downstream of said pump unit P (FIG. 2) there is located the above-mentioned check valve 8 (FIG. 3) which may be of any convenient type but here comprises a generally tubular housing 61 having a valve seat 63 for cooperating with the valve 64. An O-ring 66 or the like is associated with said valve for insuring snug sealing of the valve. An internal guide 67 is threadedly fixed at 68 to the housing 61 for supporting and guiding the stem 69 of said valve and also for supporting and guiding the spring 71 which bears against the annular flange 72 on said valve for urging same toward a closed position. As is conventional, the internal guide 67 may be rotated with respect to the housing 61 for advancing or retracting same along said threaded connection whereby to select the desired compression of said spring 71.

The housing 61 (FIG. 2) is provided with suitable means, here a groove 73, to define a flange 78 which may be received into an appropriate groove 79 in said upper section 2A and clamped therein by the surface 87 on the dog 88 of portion 2B when said components 2A and 2B are assembled and fixed together. The adjacent end of the tubing 7 is fixed to the housing 61 in any desired manner as by cementing same into an appropriate recess 80. The other end of said valve is provided with a conventional means, here a sleeve 76 and O-ring 77 by which the nozzle 9 may be fixed to the other end of said check valve, as by a suitable friction fit.

The nozzle 9 may be any conventional nozzle as desired.

OPERATION

Although the operation of the apparatus has been indicated in connection with the above description, further details of such operation will be discussed hereinafter.

One or both of the containers 6 may be alternately, successively or simultaneously connected to the tubing 7 through conventional valves $V_1$ and $V_2$ as desired. The containers 6 are preferably placed sufficiently above the pump unit P to produce a suitable pressure head whereby to supply liquid from said containers to the upstream side of said pump unit. Reciprocation of the plate 38 as above described in response to rotation of the motor 12 drives the liquid in the tube 7 in the known manner of a peristaltic pump in a pulsating flow through the check valve 8 to the nozzle 9. From the nozzle, said fluid is then directed for treating purposes as desired.

By conducting performance tests of said apparatus, it has been found that a completely adequate supply of liquid is furnished to the pump chamber 37, for subsequent, satisfactory discharge through the nozzle 9, even where the pressure head is minimal. For example, the pump P was connected to one end of a tube 7 which was one foot in length and was connected at its other end to a container of liquid located at about the same level as the pump. Thus, the pressure head was only sufficient to maintain liquid in the short tube 7. Nevertheless, there was no significant difference in the discharge of liquid from the nozzle 9 when compared with the discharge produced under the conditions disclosed in FIG. 1.

It is believed that the inertia of the liquid in the supply tube 7 when compared with the resistance of the spring 71 to compression is such that the resistance of the spring is overcome before the liquid is backed up along the tube 7 when the plate 38 is moved downwardly.

More particularly, as the plate 38 is moved upwardly, a reduced pressure is instantly created in the portion of the tube 7 beneath the plate 38, thereby drawing liquid into such portion. Thus, said liquid moving through the tube 7 to fill the vacuum therein develops inertia. Accordingly, when the plate 38 is subsequently moved downwardly, the said inertia toward the nozzle must first be overcome. However, before such inertia is overcome, the valve 64 is opened and the trapped liquid is discharged through the nozzle 9.

It is thought that the attitude of the plate 38 as it is reciprocated may have some effect upon the flow of liquid through the tube 7. That is, due to the clearance between the sleeve 34 and plunger 33, the plate is permitted to move in a manner which augments the flow of liquid through the tube 7.

If for any reason it is necessary to place the container 6 at an elevation above the pump P, then a check valve similar to the check valve 8 and oriented in the same direction as the check valve 8 may be placed on the upstream side of the pump P in a known manner. However, as stated above, it has been found that where the tubing 7 is of conveniently usable length, the inertia of the liquid coupled with a relatively small head pressure in said tubing will be sufficient, with proper adjustment of the spring 71, to cause the valve 64 to open when the tubing 7 is compressed by the plate 38 without significant backing up of the liquid in the tubing 7. Thus, there will be a continuous presence of the liquid in tubing 7 adjacent the chamber 37 when the pump plate is moved in its suction (upward) stroke.

It will be observed that the pump unit here described is readily portable, is easily disassembled to remove contaminated parts and has no contact at all with the liquid being pumped. Thus, when changing from one liquid to another, or from one location of use to another, it may be unnecessary to sterilize the entire pump structure. That is, it may be sufficient only to sterilize or replace the tubing and parts associated therewith through which liquid flows, namely, the fitting at the container end of said tubing, the check valve and the nozzle. The pump is of sufficient mechanical simplicity as to be virtually maintenance free and by utilizing an air-driven motor, there is eliminated the necessity for special protective features which are usually required where electrical equipment is used in an operating room.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are as defined as follows:

1. A manually manipulable pump unit for effecting a pulsating flow of liquid to a point of treatment in an operating or other surgically related room, the combination comprising:
   a housing having an elongated opening therethrough for the reception therethrough of a resilient flexible tubing;
   a hollow pedestal upstanding from said housing and a generally elongated tubular handle fixed to the upper end of said pedestal and having its centerline lying in a plane generally parallel with the centerline of the opening in said housing;
   a rotary prime mover within said handle and link means within said pedestal driven by said motor for effecting reciprocal motion in a direction generally perpendicular to the centerline of said opening;
   a plate within said opening engageable against tubing within said opening and caused to move toward and away from the opposite side of said opening by said link means in response to actuation of said motor;
   whereby said tubing will be ultimately squeezed and released for effecting a pulsating flow through said tubing in the manner of a peristaltic pump.

2. The device of claim 1 including also a volumetric control valve within said housing, said control valve comprising:
   a plate adjacent one side of said opening and movable toward and away from the opposite wall thereof and manually manipulable threaded means for effecting movement of said plate toward and away from said opposite wall.

3. The device of claim 1 wherein said prime mover is an air-driven motor and including also speed changing means driven by said motor and an eccentric driven by the output of said speed changing means, said eccentric being connected for effecting reciprocation of said link means.

4. The device of claim 1 including a stem upstanding from said pump plate and a bushing at least within said housing for reciprocally guiding said stem, said link means being connected to the upper end of said stem for effecting reciprocation thereof and thereby effecting reciprocation of said pump plate toward and away from the said opposite side of said opening.

5. The device of claim 1 wherein said housing is split generally longitudinally thereof to facilitate insertion and removal of tubing into and out from said opening and manually operable means for connecting and disconnecting the components of said housing with respect to each other.

6. The device of claim 5 wherein said manual means comprise a quick connect and disconnect means.

7. The device of claim 5 wherein the components of said housing are provided with interfitting lug and recess means for associating same detachably together and means including threaded means operable to hold said components against movement with respect to each other in a detaching direction.

8. The device of claim 5 wherein the split relationship of said housing divides said opening for permitting said tubing to be inserted into said opening by a movement radially thereof.

9. The device of claim 5 wherein said housing is longitudinally split on offset planes whereby to define at least one pair of mating surfaces aligned perpendicularly to the centerline of said opening, said surfaces being provided with interfitting lug and recess means for holding said components together, in one portion of one of said components said central opening being of generally U-shaped cross section opening against a generally planar surface of the other of said components and in another portion the other of said components defining a generally U-shaped cross section opening against a planar surface of said one component and manually attachable and detachable means when attached with said lug and recess means interengaging each other for preventing movement of said components with respect to each other in a lug and recess detaching direction.

10. The device of claim 1 in which said tubing is connectible to a source of liquid on the upstream side of said pump for supplying liquid thereto at a pressure head sufficient to maintain liquid in said tubing upstream of said plate, and including a check valve connected in series with said tubing on the downstream side of said pump unit and resiliently urged to a closed position, said check valve being oriented to permit downstream flow therethrough upon overcoming said resilient urging, but to block diverse flow therethrough.

* * * * *